US005369092A

United States Patent [19]

Blakeway et al.

[11] Patent Number: 5,369,092
[45] Date of Patent: Nov. 29, 1994

[54] ODORANT COMPOSITIONS

[75] Inventors: John M. Blakeway, Nucourt; Francoise Sauvage, Bois-Colombes, both of France

[73] Assignee: Givaudan-Roure Corporation, Clifton, N.J.

[21] Appl. No.: 50,438

[22] PCT Filed: Sep. 17, 1992

[86] PCT No.: PCT/EP92/02141
§ 371 Date: Jul. 1, 1993
§ 102(e) Date: Jul. 1, 1993

[87] PCT Pub. No.: WO93/05761
PCT Pub. Date: Apr. 1, 1993

[30] Foreign Application Priority Data

Sep. 23, 1991 [XH] Hague Agreement .......... 91116114.9

[51] Int. Cl.$^5$ ............................................. A61K 7/46
[52] U.S. Cl. ............................................. 512/2; 512/3
[58] Field of Search ............................................. 512/2, 3

[56] References Cited

U.S. PATENT DOCUMENTS 4,292,211  9/1981  Herman ................................... 512/2
4,857,321  8/1989  Thomas ................................. 514/858

FOREIGN PATENT DOCUMENTS 0126483  11/1984  European Pat. Off. ................ 512/2
2224127  10/1974  France .................................... 512/2
2588756   4/1987  France .................................... 512/2

OTHER PUBLICATIONS

Courtin, Chem. Abst; vol. 108, #226,675; (1988).
Malik et al., Chem. Abst.; vol. 115, #286,956f (1991).
Derwent Abstract No. 84–295900 of European Patent No. 126,483 (May 1984).
Derwent Abstract No. 87–151916 of Franch Patent No. 2,588,756 (Apr. 1987).
Derwent Abstract No. 75–07945W of France Patent No. 2,224,127 (Oct. 1974).

*Primary Examiner*—James H. Reamer

[57] ABSTRACT

Novel odorant compositions comprising ethanol, perfume concentrate and panthenol.

14 Claims, No Drawings

ODORANT COMPOSITIONS

The present invention is concerned with novel odorant compositions. More particularly, the invention is concerned with novel odorant compositions with prolonged diffusion after the application on the skin.

It is well known that mixtures of perfume materials when deposited on the skin lose intensity and may change character with time, mainly due to factors such as differential evaporation and skin penetration.

Many attempts have been made to minimize these drawbacks, but so far without notable success. Particularly, efforts have been made to prolong the diffusion, as well as to improve other characteristics of perfume materials, by e.g. increasing the perfume concentrate concentration or by using additives such as silicones, glycerol, polyethylene glycols and so on. Such perfume compositions, however, have never been really successful as the results obtained were only marginal.

It thus actually existed a problem in this connection, which now has been overcome by the present invention.

Surprisingly, it has now been found that the addition of panthenol significantly improves and particularly prolongs diffusion of perfume materials from the skin, without notably modifying the olfactive note of the product. The present invention thus concerns odorant compositions comprising from about 70 to about 99% of ethanol, from about 0.5 to about 30% of perfume concentrate, from about 0.1 to about 20% of panthenol and from about 0% to about 30% of water.

The term "odorant composition", as used in connection with this invention, means solutions of perfume materials in alcohol and stands for well known commercial products such as e.g. Deo-Cologne, Eau de Cologne, Eau de Toilette, Perfume Extrait and so on.

The term "perfume concentrate" stands for the required mixture of perfume materials of synthetic and/or natural origin.

The term "panthenol" as used in connection with the present invention stands for DL-panthenol or for D-panthenol.

The percentages referred to in the scope of the present invention are on a weight by weight basis.

The amount of perfume concentrate and thus also the amount of ethanol present depends upon the respective odorant composition and can be easily determined by the skilled artisan. The amount of panthenol can also vary within a range of from about 0.1 to about 20%, but lies preferably in the range of from about 0.5 to about 5%. By way of examples, in the following odorant composition the respective ingredients may be present in the following approximate amounts:

| a) Deo-Cologne: | |
| --- | --- |
| Perfume concentrate | 0.5–3% |
| Panthenol | 0.5–2% |
| Ethanol (98°) | q.s. |
| b) Eau de Cologne: | |
| Perfume concentrate | 2–7% |
| Panthenol | 0.5–3% |
| Ethanol (88° or 73°) | q.s. |
| c) Eau de Toilette: | |
| Perfume concentrate | 5–20% |
| Panthenol | 0.5–5% |
| Ethanol (93°) | q.s. |
| d) Perfume Extrait: | |
| Perfume concentrate | 15–25% |
| Panthenol | 0.5–5% |
| Ethanol (96°) | q.s. |

With the alcohol also water is introduced into the compositions, and the degrees of alcohol mean % v/v at 20° C.

Besides the ingredients mentioned before, the odorant compositions according to the present invention can also contain additives which are well known in the art. By way of example the following can be mentioned: colorants, UV-absorbants, antioxydants, preservatives, emollients, natural herbal extracts, germicides, deodorants and so on. If such additions are present their amount lies preferably between about 0.05 and about 2%.

Furthermore, the odorant compositions can also contain vitamins, such as e.g. vitamin E, preferably in the form of the acetate, vitamin A, preferably in the form the acetate or any other common ester, vitamin C, preferably in the form of the palmitate, and so on.

The following examples are illustrative of the present invention and are by no means intended to limit the scope of the present invention.

EXAMPLE 1

In a manner known per sea Deo-Cologne of the following composition has been prepared:

| Perfume concentrate | 1% |
| --- | --- |
| D-Panthenol | 1% |
| Ethanol (96°) | 98% |

EXAMPLE 2

In a manner known per se an Eau de Cologne of the following composition has been prepared:

| Perfume concentrate | 5% |
| --- | --- |
| D-Panthenol | 2% |
| Ethanol (90°) | 93% |

EXAMPLE 3

In a manner known per se an Eau de Toilette of the following composition has been prepared:

| Perfume concentrate | 10% |
| --- | --- |
| D-Panthenol | 2% |
| Ethanol (96°) | 88% |

EXAMPLE 4

In a manner known per sea Perfume Extrait of the following composition has been prepared:

| Perfume concentrate | 25% |
| --- | --- |
| D-Panthenol | 3% |
| Ethanol (96°) | 73% |

In order to determine the efficacy of claimed odorant compositions the compositions according to Examples 2, 3 and 4 have been compared to analogous compositions containing no panthenol. The respective compositions were applied during several days to the left and the right arm of test persons who had then to identify which compositions have the longer diffusion after application and by how much the diffusion was extended. The results are summarized in the enclosed tables.

TABLE 1

| Nummber of test persons | Composition according to Example | Percentage of test persons having identified the odorant composition on containing panthenol to diffuse longer |
| --- | --- | --- |
| 34 | 2 | 97% |
| 28 | 3 | 93% |
| 14 | 4 | 100% |

TABLE 2

| Eau de Toilette of Examples 3 | Number of test persons | Number of test persons finding diffusion lasting | | |
| --- | --- | --- | --- | --- |
| | | <4 hours | 4–5 hours | >5 hours |
| with D-Panthenol | 50 | 6 | 30 | 14 |
| without D-Panthenol | 50 | 25 | 21 | 4 |

We claim:

1. Odorant composition in the form of solutions and exhibiting prolonged diffusion after application on the skin, said odorant composition comprising from about 70 to about 99% of ethanol, from about 0.5 to about 30% of perfume concentrate, from about 0.1 to about 20% of panthenol and from about 0% to about 30% of water.

2. Odorant composition according to claim 1 comprising from about 0.5 to about 3% of perfume concentrate and from about 0.5 to about 2% panthenol.

3. Odorant composition according to claim 1 comprising from about 2 to about 7% of perfume concentrate and from about 0.5 to about 3% of panthenol.

4. Odorant composition according to claim 1 comprising from about 5 to about 20% of perfume concentrate and from about 0.5 to about 5% panthenol.

5. Odorant composition according to claim 1 comprising from about 15 to about 25% of perfume concentrate and from about 0.5 to about 5% of panthenol.

6. Odorant composition according to claim 2 which is in the form of a Deo Cologne.

7. Odorant composition according to claim 3 which is in the form of an Eau de Cologne.

8. Odorant composition according to claim 4 which is in the form of an Eau de Toilette.

9. Odorant composition according to claim 5 which is in the form of a Perfume extrait.

10. A method for providing, enhancing, or modifying the prolonged diffusion of an odorant composition applied to the skin which comprises adding thereto from about 0.1 to about 20% of panthenol.

11. A method according to claim 10 wherein said composition is a Deo Cologne, and there is added from about 0.5 to about 2% of panthenol.

12. A method according to claim 10 wherein said composition is an Eau de Cologne, and there is added from about 0.5 to about 3% of panthenol.

13. A method according to claim 10 wherein said composition is an Eau de Toilette or a Perfume extrait, and there is added from about 0.5 to about 5% of panthenol.

14. A method for improving and prolonging the diffusion of perfume materials from the skin in which the perfume materials contain ethanol, comprising adding panthenol to said perfume materials, the panthenol being added in an amount sufficient to prolong perfume material diffusion.

* * * * *